(12) United States Patent
Wilson

(10) Patent No.: US 6,630,452 B2
(45) Date of Patent: Oct. 7, 2003

(54) NUTRITIONAL FORMULATION CONTAINING PREBIOTIC SUBSTANCES

(75) Inventor: Jeffrey L. Wilson, Upper Darby, PA (US)

(73) Assignee: Wyeth, Madison, NJ (US)

(*) Notice: Subject to any disclaimer, the term of this patent is extended or adjusted under 35 U.S.C. 154(b) by 209 days.

(21) Appl. No.: 09/778,257

(22) Filed: Feb. 7, 2001

(65) Prior Publication Data

US 2003/0060445 A1 Mar. 27, 2003

Related U.S. Application Data

(60) Provisional application No. 60/198,211, filed on Feb. 17, 2000.

(51) Int. Cl.$^7$ ....................... A61K 31/70; A61K 31/715
(52) U.S. Cl. ............................. 514/25; 514/54
(58) Field of Search ...................... 514/25, 54

(56) References Cited

U.S. PATENT DOCUMENTS

| 5,514,660 A | 5/1996 | Zopf et al. |
| 5,753,630 A | 5/1998 | Zopf et al. |
| 5,883,079 A | 3/1999 | Zopf et al. |

FOREIGN PATENT DOCUMENTS

| CN | 1129524 A | 8/1996 |
| WO | WO94/18986 A | 9/1994 |
| WO | WO97/02830 A | 1/1997 |
| WO | WO98/31241 A | 7/1998 |
| WO | WO99/64022 A | 12/1999 |
| WO | WO00/10402 A | 3/2000 |

OTHER PUBLICATIONS

Mitsuoka et al, "Effect of Fructo–oligosaccharides on Intestinal Microflora", *Die Nahrung*, 31, 5–6: 427–436 (1987).

Bouhnik et al, "Short Chain Fructo–oligosaccharide Administration Dose–Dependently Increase Fecal Bifidobacteria In Healthy Humans", *J. Nutrition*, 129: 113–116.

Gibson et al, "Selective Stimulation of bifidobacteria in the Human Colon, by Oligofructose and Inulin", *Gastroenterology*, 108: 975–982 (1995).

Idota et al, "Inhibition of Cholera Toxin by Human Milk Fractions and Sialyllactose," *Infection and Immunity*, 750–757 (1997).

Simon et al, "Inhibition of Helicobacter pylori Binding to Gastrointestinal Epithelial Cells by Sialic Acid–Containing Oligosaccharides," *Infection and Immunity*, 750–757 (1997).

*Primary Examiner*—Zohreh Fay
(74) *Attorney, Agent, or Firm*—Michael R. Nagy

(57) ABSTRACT

A nutritional composition is provided which comprises oligofructose and sialyllactose.

14 Claims, 3 Drawing Sheets

NUTRITIONAL FORMULATION CONTAINING PREBIOTIC SUBSTANCES

CROSS REFERENCE TO RELATED APPLICATIONS

This application claims the benefit of U.S. Provisional Application No. 60/198,211) which was converted from U.S. application Ser. No. 09/506,009, filed Feb. 17, 2000.

FIELD OF THE INVENTION

This invention relates to nutritional formulations containing prebiotic substances and the use of such formulations in the growth promotion of beneficial microorganisms and the inhibition of pathogenic organisms. More specifically, this invention relates to nutritional formulations containing oligofructose and sialyllactose.

BACKGROUND OF THE INVENTION

Oligofructose is a series of natural oligosaccharides found primarily in vegetables, such as onion and the root of the chicory plant. Oligofructose is known to be a specific substrate for Bifidobacteria. (See, e.g., Mitsuoka et al, "Effect of Fructo-oligosaccharides on Intestinal Microflora", *Die Nahrung*, 3, 5–6: 427–436 (1987)).

Oligofructose passes through the small intestine without being digested, reaching the large intestine. In the large intestine, oligofructose is fermented only by a limited range of microorganisms that include most species of Bifidobacteria, i.e., species of bacteria beneficial for human health. (See Bouhnik et al, "Short Chain Fructo-Oligosaccharide Administration Dose-Dependently Increases Fecal Bifidobacteria in Healthy Humans," *J. Nutrition*, 129:113–116).

For example, oligofructose can be utilized efficiently by Lactobacilli and Bifidobacteria. It is known that in mixed populations of bacteria such as that which exists in the human colon, oligofructose is consumed preferentially by Bifidobacteria. The other bacteria present in this "mixed population" either do not grow or are inhibited from growing. (See, e.g., Gibson et al, "Selective Stimulation of Bifidobacteria in the Human Colon, by oligofructose and Insulin." *Gastroenterol*, 108:975–982 (1995)).

Moreover, it is known that a metabolic by-product of Bifidobacteria is short chain fatty acids, resulting in a reduction of the pH in the digestive tract. This pH effect has been observed clinically and documented in Mitsuoka et al, "Effect of Fructo-oligosaccharides on Intestinal Microflora", *Die Nahrung*, 3,5–6: 427–438 (1987).

Sialyllactoses are oligosaccharides which occur naturally in human milk as well as in milk of other mammals. However, sialyllactoses are present at noticeably higher concentrations in human milk compared to other mammalian species.

The two primary species of sialyllactose are 3'-sialyllactose and 6'-sialyllactose. These species occur naturally in human milk at a relative ratio of 1:3 (3':6'). Sialyllactose is known to have anti-adhesive properties for specific pathogenic bacteria. For example, it has been suggested that sialyllactose acts to inhibit cholera toxin (see, Idota et al, "Inhibition of Cholera Toxin by Human Milk Fractions and Sialyllactose," *Biosci. Biotech. Biochem.* 59:417–419) and *Helicobacter pylori* (see, Simon et al, "Inhibition of *Helicobacter pylori* Binding to Gastrointestinal Epithelial Cells by Sialic Acid-Containing Oligosaccharides," *Infection and Immunity*, 750–757, (1997)). In light of its antiadhesive properties, sialyllactose has been used to treat a number of medical conditions. For example, U.S. Pat. Nos. 5,514,660 and 5,753,630, describe the use of sialyllactose in the treatment and inhibition of duodenal ulcers. U.S. Pat. No. 5,883,079 describes the use of sialyllactose to inhibit *H. pylori* infection in mammalian tissue.

However, the use of two prebiotic substances, specifically, oligofructose and sialyllactose, in combination has heretofore not been described. Accordingly, it can be seen that there is a need for such a combination.

SUMMARY OF THE INVENTION

The present invention is related to a nutritional composition, which is effective in increasing beneficial Bifidobacteria and inhibiting the binding of pathogenic microorganisms to human tissue. More specifically, the present invention is directed to nutritional compositions comprising oligofructose and sialyllactose. The present invention is further directed to a method of increasing the concentration of Bifidobacteria and inhibiting the binding of pathogenic bacteria in a human subject comprising enterally administering to said subject a composition comprising oligofructose and sialyllactose.

DETAILED DESCRIPTION OF THE INVENTION

Figure 1:
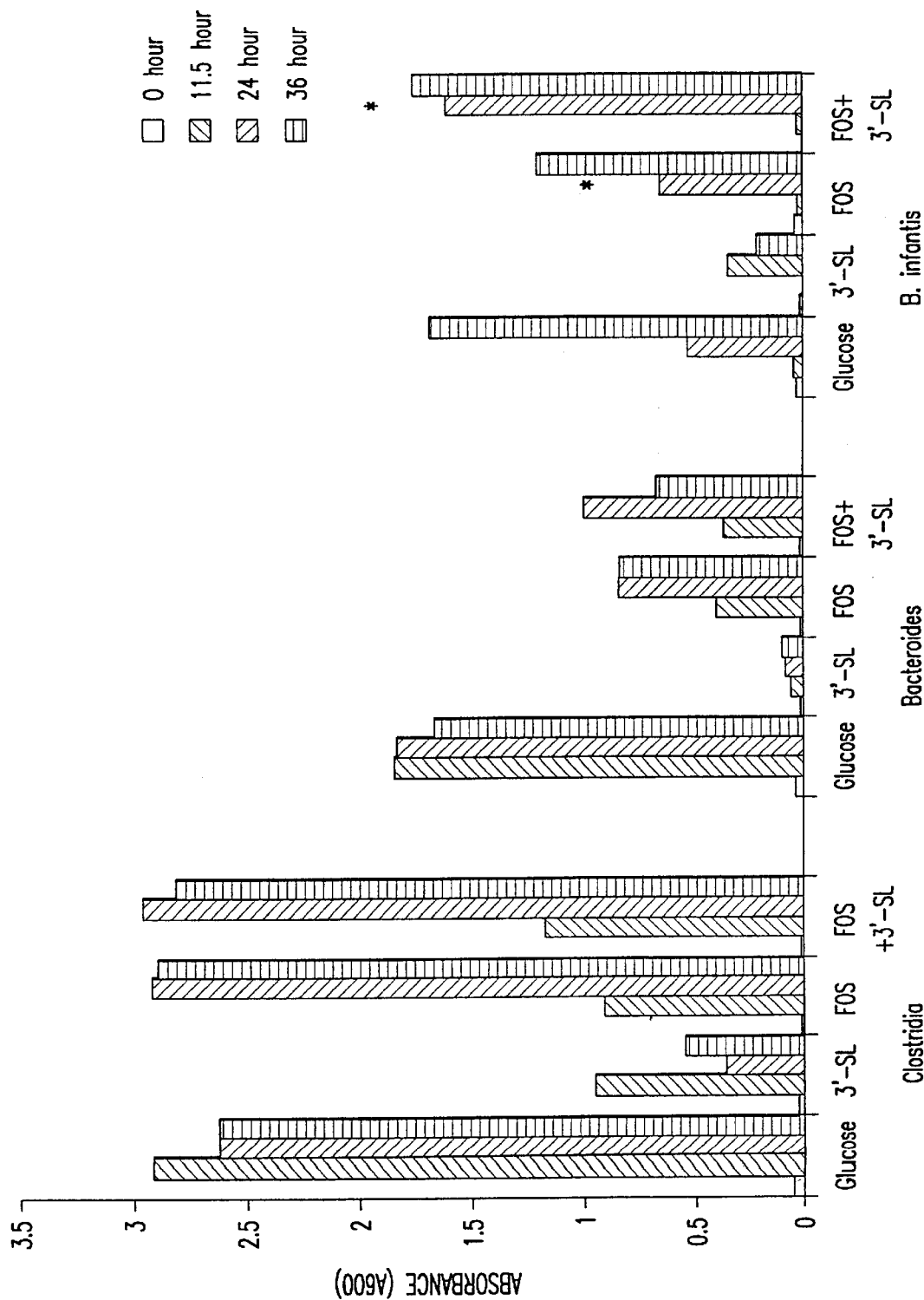
FIG. 1 shows the growth of Bifidobacteria, Clostridia and Bacteroides as set forth in Example 1.

The sialyllactose useful in the present compositions comprises a mixture of 3'-siallylactose and 6'-siallyllactose. Preferably, the sialyllactose used herein is 3'-siallylactose. The sialyllactose useful in the present compositions may be prepared according to any of the methods described, e.g., in U.S. Pat. Nos. 5,575,916; 5,714,075; 5,278,299; 5,374,541; and 5,876,980. However, it will be recognized by those skilled in the art that any other known method of synthesizing and purifying sialyllactose may be used to prepare the sialyllactose, useful in the present compositions.

The oligofructose component of the present composition may be prepared from a naturally occurring polyfructose (inulin) which may be found in many plants, including onions, leeks, wheat, chicory and artichoke. Chicory is most commonly used. Oligofructose can be recovered in sufficient quantities, from these plants, by methods known in the art. The naturally occurring inulin comprises oligofructose and higher polymers of fructose. The inulin can be separated as it is soluble in hot water. If desired, the naturally occurring oligofructose can be separated as it is additionally soluble in cold water. The inulin, optionally after removal of the naturally occurring oligofructose, may be converted into oligofructose by hydrolysis. The inulin may be broken down into oligomeric chain lengths by using an inulase enzyme. Inulin can also be degraded into oligomeric chain lengths by chemical hydrolysis. The oligofructose component of the present composition may also be prepared by synthesis rather than by extraction procedures. Oligofructose may be synthesized from sucrose by transfructosylation, which is accomplished by means of an enzyme, β-fructofuranosidase, that links additional fructose monomers to the sucrose molecule. Oligofructose formed in this manner contains fructose units linked to a terminal glucose unit. Oligofructose derived from inulin from plants such as chicory contains both fructose chains and fructose chains with a terminal glucose unit. Oligofructose prepared by methods such as these is commercially available. A preferred form of oligofructose for purposes of this invention is Raftilose® available from Orafti S.A., Tienen, Belgium. Again, it is understood that any known method of synthesizing and/or isolating oligofructose may be suitable for the present invention.

The nutritional composition of the present invention may comprise 0.1 g/L to 10 g/L of oligofructose and 6 mg/L to 10 g/L of sialyllactose. Preferably, the present composition contain 0.3 g/L to 6 g/L of oligofructose and 60 mg/L to 1 g/L of sialyllactose, more preferably 1 g/L to 3 g/L of oligofructose and 100 mg/L to 600 ml/L of sialyllactose and even more preferably about 3 g/L of oligofructose and about 100 mg/L of sialyllactose.

The present inventors have found that the combination of oligofructose and sialyllactose in the present nutritional formulations produces a synergistic prebiotic effect, i.e., a prebiotic effect greater than the additive effect of the substances alone. The present use of oligofructose and sialyllactose specifically increases the concentration of beneficial bacteria (Bifidobacteria) in the gut while having no effect on pathogenic bacteria (e.g., Clostridia, Bacteroides, *E. coli*, etc). In addition, although. the administration of oligofructose is known to lower the pH of its environment, the combination of oligofructose with sialyllactose has been found to lower the pH to an even greater extent. This reduction in gut pH results in an environment which is less conducive to the growth of certain organisms, specifically, the less beneficial or more pathogenic bacteria such *E. coli* or Bacteroides.

The nutritional compositions of the present invention can be utilized in conjunction with various nutritional products, such as infant formula, follow-on formula, toddler's beverage, milk, yogurt, fruit-based products for older children (such as fruit juices) candies, chewing gum, lozenges, powders, tablets, etc. Preferably the present compositions are added to infant formula. The infant formula can be in the form of a ready to feed liquid or a powder, which may be mixed with water and fed to the infant. It is most preferred that the present formulation be added to infant formula in liquid form.

Infant formula suitable for use with the present invention should contain all vitamins and minerals considered to be essential in the daily diet. These vitamins and minerals should be present in nutritionally significant amounts. Examples of vitamins, minerals and other nutrients which may be included in infant formulas in which the present formulations are to be added include vitamin A, vitamin B complex, vitamin C, vitamin D, vitamin E, vitamin K, calcium, magnesium sodium, potassium, phosphorous, copper, zinc, chloride, iodine, selenium, iron, niacin, folic acid, pantothenic acid, biotin, chlorine, Inositol and manganese.

The infant formula may contain one or more lipid sources as will be recognized by those skilled in the art. The infant formula may further contain other substances than to have a beneficial effect, such as, nucleotides, immunoglobulins, polyunsaturated fatty acids, etc.

A preferred infant formula according to the present invention is as follows:

| Ingredient | Units | Per Liter |
|---|---|---|
| Energy | Kcal | 672 |
| Protein | g | 15 |
| Whey: Casein ratio | | 60:40 |
| Fat | g | 36 |
| Carbohydrate | g | 72 |
| Oligofructose | g | 3.0 |
| Sialyllactose | mg | 100 |
| Vitamin A | RE | 750 |
| Mixed natural carotids | IU | 400 |
| Vitamin D | mcg | 10.6 |
| Vitamin F | mg | 7.4 |
| Vitamin K | mcg | 67.0 |
| Vitamin $B_1$ (thiamin) | mcg | 1000 |
| Vitamin $B_2$ (riboflavin) | mcg | 1500 |
| Vitamin $B_6$ (pyridoxine) | mcg | 600 |
| Vitamin $B_{12}$ (cyanacobalmine) | mcg | 2.0 |
| Niacin | mcg | 9.0 |
| Folic Acid | mcg | 80 |
| Pantothenic Acid | mcg | 3000 |
| Biotin | mcg | 90 |
| Vitamin C (ascorbic acid) | mg | 90 |
| Choline | mg | 100 |
| Inositol | mg | 33 |
| Calcium | Mg | 460 |
| Phosphorous | Mg | 333 |
| Magnesium | Mg | 64 |
| Iron | Mg | 8.0 |
| Zinc | Mg | 6.0 |
| Manganese | mcg | 50 |
| Copper | mcg | 560 |
| Iodine | mcg | 100 |
| Sodium | mg | 160 |
| Potassium | mg | 650 |
| Chloride | mg | 433 |
| Selenium | mcg | 14 |

The present invention is further described with reference to the following examples:

EXAMPLE 1

Identical inoculua ($A_{600}$ ▽ 1.0) of overnight cultures (PYG broth, 37° C., anaerobic) of each organism (Clostridia, Bacteroides, or *B. lactis*) were grown in batch culture (37° C., anaerobic) with constant stirring. Carbohydrate-deficient batch culture media (PYG) was supplemented with either glucose (3.0 g/L), oligofructose (FOS at 3.0 g/L), sialyllactose (3'- or 6'-sialyllactose at 100 ml/L), or oligofructose plus sialyllactose (3.0 g/l and 100 mg/L, respectively). Growth was monitored at various time points (see FIG. 1) by determining the titers of the bacteria on selective agar (BIM-25 agar for Bifidobacteria and Wilkens-Chalgren agar for Clostridia and Bacteroides). Results of the growth analysis are shown in FIG. 1.

As shown in FIG. 1, substituting 3'-sialyllactose for glucose in the growth media resulted in essentially no growth of Clostridia or Bacteroides in comparison to glucose. However, the growth of Clostridia and *B. infantis*, but not Bacteroides, in the presence of oligofructose was similar to that seen in the presence of glucose. The combination of oligofructose and sialyllactose had no effect on the growth of Clostridia or Bacteroides. However, there was a noticeable effect on the growth of *B. infantis*, especially at the twenty four hour time point. It can be seen that the combination of oligofructose and sialyllactose had synergistic effect on the growth of *B. infantis*.

EXAMPLE 2

Identical inoculua ($A_{600}$ ▽ 1.0) of overnight cultures (PYG broth, 37° C. anaerobic) of *B. Lactis* were grown in batch culture (37° C. anaerobic) with constant stirring. Carbohydrate-deficient batch culture media (PYG) was supplemented with either glucose (3.0 g/L), oligofructose (3.0 g/L), or oligofructose (3.0 g/L) plus sialyllactose (3'-6'-sialyllactose at 100 ml/L). Growth was monitored at various time points (see FIG. 2) by determining the titers of the *B. lactis* bacteria on selective agar (BIM-25 agar). Results of the growth analysis are shown in FIG. 2.

Figure 2:
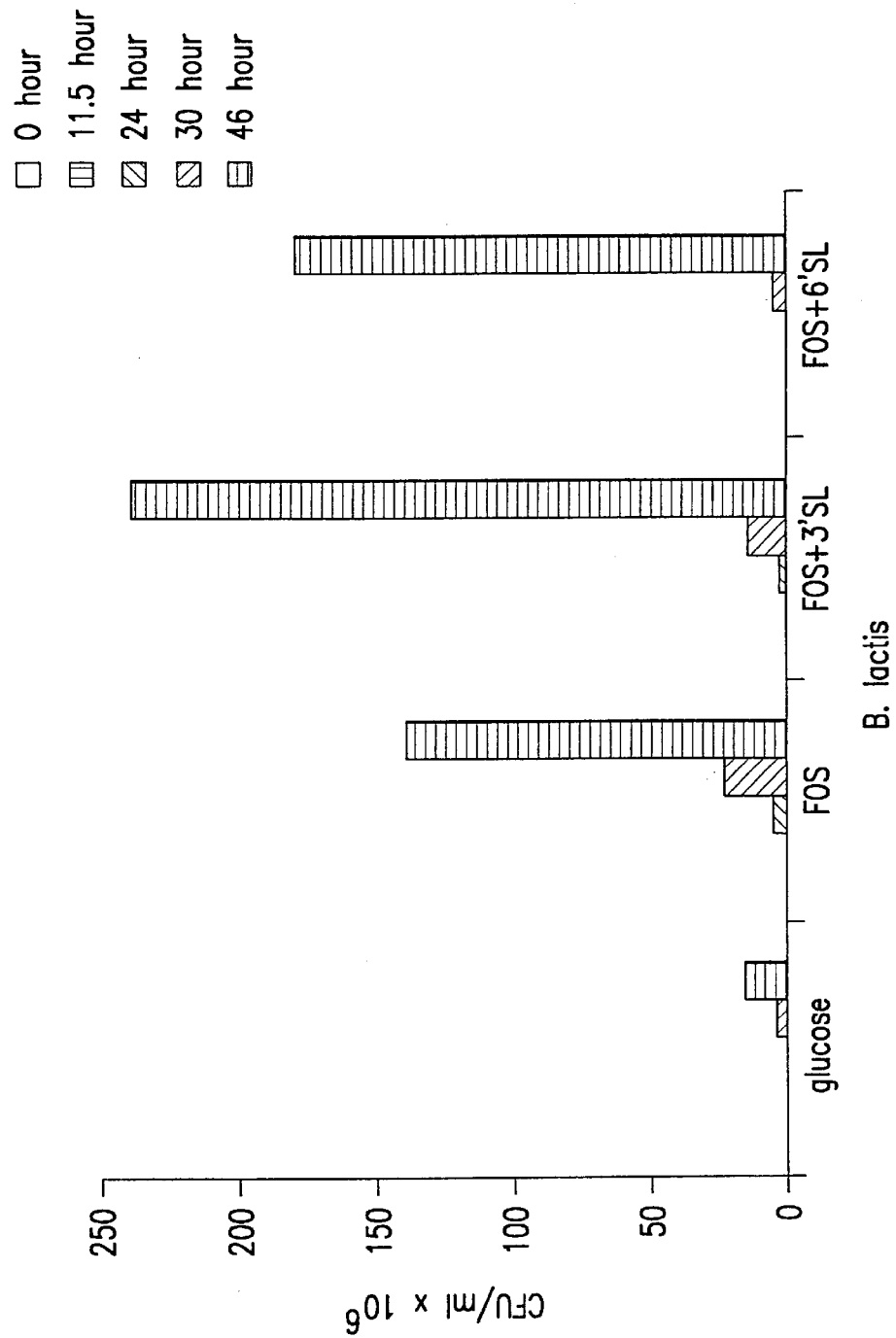
FIG. 2 shows the growth of *B. lactis* as set forth in Example 2.

FIG. 2 demonstrates that *B. lactis* grew significantly better in the presence of oligofructose than glucose. However, the growth of *Bifidobacteria lactis* was significantly enhanced in the presence of the present combination of oligofructose and either 3' or 6' sialyllactose at 46 hours.

EXAMPLE 3

A metabolic by-product of Bifidobacteria is short-chain fatty acids, the presence of which lowers the intestinal pH.

Figure 3:
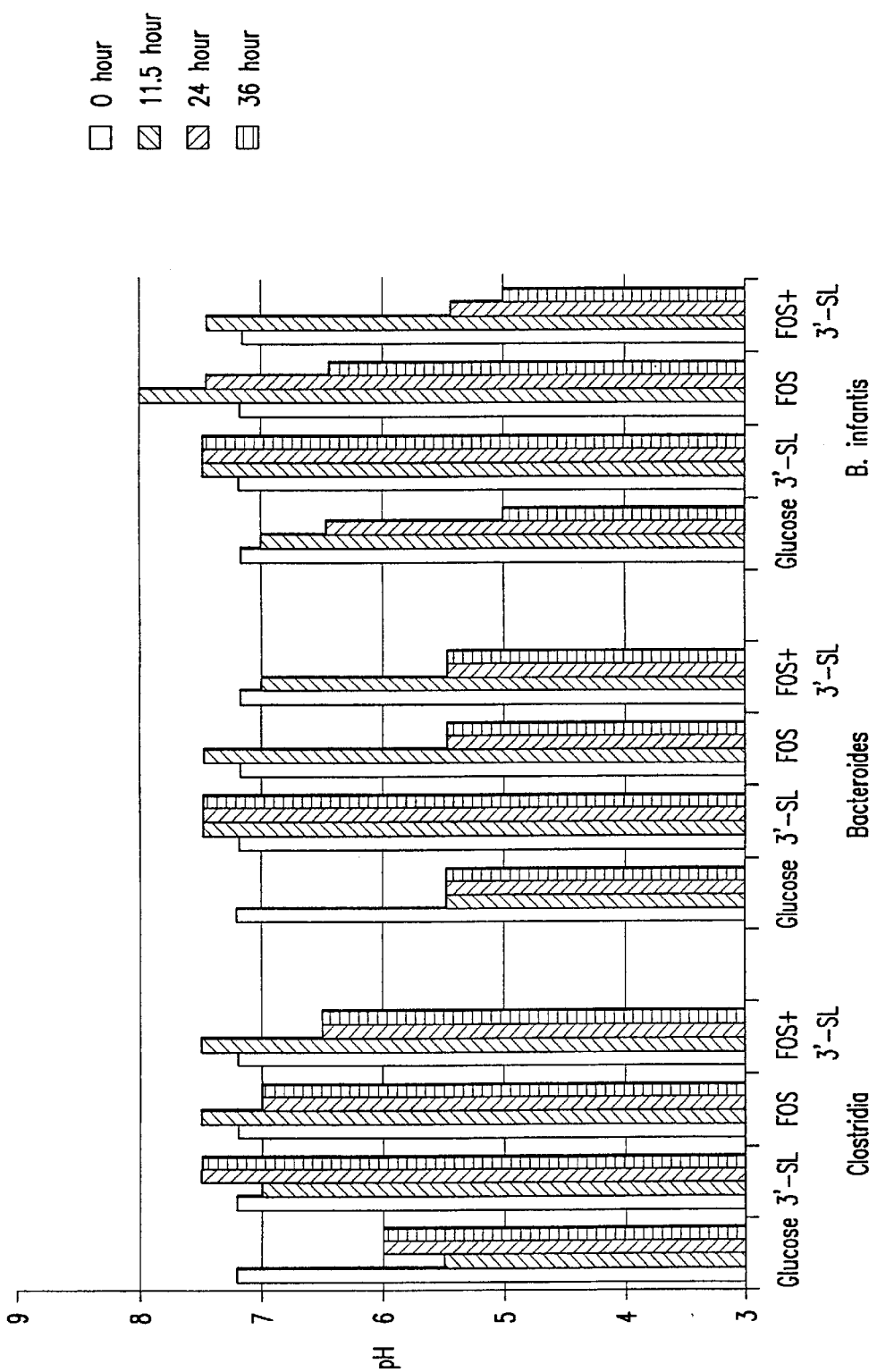
FIG. 3 shows the growth of Clostridia, Bacteroides and *B. lactis* as shown in Example 3.

FIG. 3 shows an analysis at different times post-inoculation of batch cultures of Clostridia, Bacteroides, and *B. lactis*. Identical inoculua ($A_{600} \nabla$ 1.0) of overnight cultures (PYG broth, 37° C., anaerobic) of each organism was grown in batch culture (37° C., anaerobic) with constant stirring. Carbohydrate-deficient batch culture media (PYG) was supplemented as above. The media pH were monitored at various time points. Results of the pH analysis are shown in FIG. 3.

As can be seen in FIG. 3, in the presence of glucose, all three colonic bacteria lowered the pH. In the presence of sialyllactose alone, the pH increased in all cases. This is consistent with the poor microbial growth observed in the presence of sialyllactose alone. In the presence of oligofructose, the pH lowered, but to a lesser extent than glucose in batch cultures of Clostridia and *B. infantis,* but was similar to the pH change observed in the Bacteroides culture with glucose. In the presence of the combination of oligofructose and sialyllactose of the present invention, the pH lowered to a greater extent than with glucose.

However, this reduction in pH was less than that seen with glucose (Clostridia) or similar to the glucose pH change (Bacteroides and *B. lactis*). Of particular interest is the observation that while oligofructose alone shows some pH reduction over time in the bifidobacteria culture, the presence of sialyllactose dramatically reduced the pH compared to the oligofructose-only *B. infantis* culture. Thus, the synergistic effects of oligofructose and sialyllactose are present.

The present invention may be embodied in their specific forms without departure from the spirit or essential attributes thereof and, accordingly, reference should be made to the appended claims, rather than to the foregoing specification as indicating the scope of the invention.

What is claimed is:

1. A nutritional composition comprising oligofructose and sialyllactose.

2. A composition as in claim 1, wherein the sialyllactose is a mixture of 3'-sialyllactose and 6'- sialyllactose.

3. A composition as in claim 1, wherein the sialyllactose is 3'-sialyllactose.

4. A composition as in claim 1, wherein the sialyllactose is 6'-sialyllactose.

5. A nutritional composition as in claim 2, comprising 0.1 g/L to 10 g/L of oligofructose and 6 mg/L to 10 g/L of sialyllactose.

6. A nutritional composition as in claim 5, comprising 0.3 g/L to 6 g/L of o oligofructose and 60 mg/L to 1 g/L of sialyllactose.

7. A nutritional composition as in claim 6, comprising 1 g/L to 3 g/L of oligofructose and 100 mg/L to 600 mg/L of sialyllactose.

8. A nutritional composition comprising 1.5 g/L of oligofructose and 100 mg/L of sialyllactose.

9. A nutritional composition as in claim 1, wherein said composition is in liquid form.

10. A nutritional composition as in claim 1, wherein said composition is in powder form.

11. A nutritional composition as in claim 1, further comprising a least one of Vitamin A, Vitamin D, Vitamin E, and Vitamin B complex.

12. A nutritional composition as in claim 1, further comprising at least one of calcium, magnesium, sodium, potassium, phosphorous, copper, zinc, iodine, selenium, and iron.

13. A nutritional composition as in claim 1, which is in the form of an infant formula, follow-on formula, toddler's beverage, milk yogurt, fruit juice, fruit-based drink, candy, chewing gum, or a lozenge.

14. A method of increasing the amount of Bifidobacteria and inhibiting the binding of pathogenic bacteria in a human, comprising administering to said human nutritional composition comprising oligofructose and sialyllactose.

* * * * *